United States Patent
Lee et al.

(10) Patent No.: US 11,331,402 B2
(45) Date of Patent: May 17, 2022

(54) SOLID AROMATIC COMPOSITION AND METHOD FOR MANUFACTURING SAME

(71) Applicant: MASSCON CO., LTD., Seoul (KR)

(72) Inventors: Yongeui Lee, Gyeonggi-do (KR); Min Young Cheong, Gyeonggi-do (KR); Chang Bin Lee, Busan (KR)

(73) Assignee: MASSCON CO., LTD., Seoul (KR)

( * ) Notice: Subject to any disclaimer, the term of this patent is extended or adjusted under 35 U.S.C. 154(b) by 0 days.

(21) Appl. No.: 17/252,984

(22) PCT Filed: Jun. 13, 2019

(86) PCT No.: PCT/KR2019/007116
§ 371 (c)(1),
(2) Date: Dec. 16, 2020

(87) PCT Pub. No.: WO2020/017762
PCT Pub. Date: Jan. 23, 2020

(65) Prior Publication Data
US 2021/0113731 A1    Apr. 22, 2021

(30) Foreign Application Priority Data

Jul. 19, 2018 (KR) .................. 10-2018-0084096

(51) Int. Cl.
*A61L 9/012* (2006.01)
(52) U.S. Cl.
CPC .................................. *A61L 9/012* (2013.01)
(58) Field of Classification Search
CPC ..................................................... A61L 9/012
See application file for complete search history.

(56) References Cited

U.S. PATENT DOCUMENTS

2004/0247895 A1* 12/2004 Dreja ................. C11D 3/38672
428/446

FOREIGN PATENT DOCUMENTS

| JP | 2005-523093 A | 8/2005 |
|----|---------------|--------|
| KR | 10-1992-0009416 A | 6/1992 |
| KR | 10-1999-0058712 A | 7/1999 |
| KR | 10-2000-0026387 A | 5/2000 |

(Continued)

OTHER PUBLICATIONS

English Machine Translation for KR2003-0043303 A Obtained Sep. 28, 2021 at: http://translationportal.epo.org/emtp/translate/?ACTION=claims-retrieval&COUNTRY=KR&ENGINE=google&FORMAT= (Year: 2003).*

(Continued)

*Primary Examiner* — Arrie L Reuther
(74) *Attorney, Agent, or Firm* — Christensen Fonder Dardi; Andrew H. Auderieth; Peter S. Dardi

(57) ABSTRACT

The present invention relates to a solid aromatic composition capable of significantly improving the loading rate of fragrance substances, selectively loading fragrance that can be acquired during the aging procedure of blended fragrance substances, maintaining fragrance from the early stage of the loading, and improving the persistence of fragrance to have constant intensity. Furthermore, the solid aromatic composition can resolve the problem of harmfulness to the human body by reducing a powder flying phenomenon, and can be applied to various environments by improving high-temperature stability.

13 Claims, 3 Drawing Sheets

(56) References Cited

FOREIGN PATENT DOCUMENTS

| KR | 10-2003-0043303 A | 11/2004 |
|---|---|---|
| KR | 10-2006-0046962 A | 9/2006 |
| KR | 10-2007-0072705 A | 7/2007 |
| WO | 03-089561 A2 | 10/2003 |

OTHER PUBLICATIONS

International Search Report for Patent Application No. PCT/KR2019/007116 dated Sep. 11, 2019.

* cited by examiner

SOLID AROMATIC COMPOSITION AND METHOD FOR MANUFACTURING SAME

CROSS REFERENCE TO RELATED APPLICATIONS

This application is a National Stage filing of PCT Application No. PCT/KR2019/007116 filed Jun. 13, 2019, entitled "Solid Aromatic Composition And Method For Manufacturing Same", which claims priority to Korean Patent Application No. KR 10-2018-0084096 filed Jul. 19, 2018, both of which are incorporated herein by reference.

BACKGROUND OF THE INVENTION

1. Field of the Invention

The present invention relates to a solid fragrance composition having a high load rate of a fragrant material.

In addition, the present invention relates to a solid fragrance composition which can delay or stop aging in order to achieve a desired fragrance at a specific stage during combining fragrant materials and can improve retention of fragrance and persistence of fragrance while suppressing deterioration of loaded fragrance.

In addition, the present invention relates to a solid fragrance composition suppressing a powder flying phenomenon.

In addition, the present invention relates to a method for manufacturing the solid fragrance composition as described above.

2. Description of the Related Art

Fragrances can change emotions of animals including humans, and are also used in aromatherapy to improve mental and physical health with a feeling of relief, pleasure, tension, arousal, meditation, etc. Fragrances can be provided in the form of perfumes, scented candles, diffusers, etc. In order to meet the needs of consumers, there is a growing trend of specialized stores for commercializing, such as forming perfume containers or scented candles in the shape of animals, foods, film characters, etc., for example.

In general, the fragrance composition emits fragrance into the atmosphere by using a diffuser to replenish a bottle with a fragrant substance such as oil, spraying or dropping a fragrant substance on gypsum, etc., or dropping or mixing a small amount of fragrant substance on a solid support such as scented candles.

However, the replenishing the bottle with oil may result in loss of oil and damage to the bottle. The use of gypsum may result in a problem of powder flying. In the case of scented candles, there is a risk of fire due to the necessity of ignition. In addition, since the fragrance components have different degrees of volatilization, there are common problems in that the initial fragrance can be easily deteriorated without a long lasting, due to preferential volatilization of the fragrance components having high volatility. In addition, in the spraying or dropping a fragrant substance on gypsum, etc., the use time is very short as the fragrance disappears quickly due to a low content of the fragrant material, and there is an inconvenience of repeatedly spraying or dropping.

In general, in order to achieve the desired fragrance by using a liquid fragrant material (perfuming), the steps of (1) mixing selected various fragrant materials in a desired ratio, (2) aging the mixed fragrant materials, and (3) testing the fragrance after aging are performed. If the desired fragrance is not achieved in the test after aging, the step (3) should be repeated until the desired fragrance is achieved. Here, aging refers to a process in which the fragrance of the mixed fragrant materials continuously changes and is a natural phenomenon that cannot be stopped artificially. The aging period is variable for each fragrant material, but may be about 1 to 3 months on average. In other words, it takes a lot of time to achieve a desired fragrance.

Moreover, even if you want to realize the fragrance at a specific point during aging, there is a fatal problem that it is not possible to realize the desired fragrance as a product because aging is an unstoppable natural phenomenon.

In addition, in the case of conventional gel fragrances and solid fragrances, there are problems that the initial strength of fragrance is weak and the use time is extremely short due to the low load rate of fragrance. Accordingly, in order to improve emission rate of fragrance, controllability of emission rate and persistence of fragrance and to facilitate the emission of fragrance in various environments, attempts have been made to microencapsulate a liquid fragrant material by coating with a polymer or to load fragrance in a porous substance. However, it does not reach the completion of development in the commercialization stage.

Therefore, development of technology is absolutely required for fragrance-related products, such as (1) delaying or stopping aging in order to achieve a desired fragrance at a specific stage during combining fragrant materials, (2) suppressing deterioration of fragrance and improving ease of use of a liquid fragrant material and (3) improving the amount of emission of fragrance and the duration of emission time of solid fragrances.

SUMMARY OF THE INVENTION

The present invention is aimed to provide a fragrance composition having a high load rate of fragrant material, for delaying or stopping aging in order to achieve a desired fragrance at a specific stage during combining fragrant materials, and for improving retention of loaded fragrance and persistence of fragrance.

In addition, the present invention relates to a solid fragrance composition suppressing a powder flying phenomenon.

In addition, the present invention relates to a method for manufacturing the fragrance composition as described above.

In order to solve the above problems, the present invention provides a solid fragrance composition, comprising porous particles having a plurality of nanopores, a gel matrix, a super absorbent polymer, and a fragrant material contained in the nanopores of the porous particle, wherein the composition contains 0.001 to 20 parts by weight of the super absorbent polymer based on 100 parts by weight of the total of the gel matrix and the porous particles.

The composition has micro-sized voids formed by the gel matrix, and macrovoids formed by the super absorbent polymer which are larger than the micro-sized voids.

According to one embodiment, a weight ratio of the gel matrix and the porous particles may be 1:0.1 to 1:30.

According to one embodiment, the porous particles may comprise at least one selected from the group consisting of silica, zeolite, activated carbon and acrylic resin particles.

According to one embodiment, the gel matrix may comprise at least one selected from the group consisting of agar, gypsum, silicone rubber, carrageenan, gellan gum and gelatin.

According to one embodiment, the super absorbent polymer may comprise at least one selected from the group consisting of polyacrylic acid-starch graft copolymer, polyacrylic acid-polyvinyl alcohol graft copolymer, CMC (carboxymethyl cellulose) polymer, and PVA (polyvinyl alcohol) polymer.

According to one embodiment, when the gel matrix is gypsum, silicone rubber, or a mixture thereof, a weight ratio of the gel matrix and the porous particle may be 1:0.1 to 1:3.

According to one embodiment, an average particle size of the porous particle may be 1 to 100 μm.

According to one embodiment, the nanopores of the porous particle may have an average diameter of 1 to 100 nm.

According to one embodiment, the micro-sized voids formed by the gel matrix may have an average diameter of 0.1 to 100 μm.

According to one embodiment, the macrvoids formed by the super absorbent polymer may have an average diameter of 50 to 500 μm.

In addition, the voids have the fragrant material contained therein.

Another aspect of the present invention, there is provided a method for manufacturing a solid fragrance composition, comprising:

1) mixing porous particles and a gel matrix to prepare a mixture;

2) mixing a super absorbent polymer and water to prepare a water-absorbed super absorbent polymer;

3) mixing the water-absorbed super absorbent polymer of 2) with the mixture of 1);

4) injecting the mixture of 3) into a mold and curing it to prepare a molded product;

5) drying the molded product of 4) to form a support having voids formed by removing moisture from the super absorbent polymer; and 6) injecting a fragrant material into the support of 5), wherein the composition contains 0.001 to 20 parts by weight of the super absorbent polymer based on 100 parts by weight of the total of the gel matrix and the porous particles.

According to one embodiment, the load rate of the fragrant material according to Equation 1 may be 100 to 500%.

Load rate (%)=(maximum weight of loaded fragrant material (g)/weight of support (g))×100 [Equation 1]

Other specifics of the embodiments of the present invention are included in the detailed description below.

Effect of the Invention

According to the solid fragrance composition and the method for manufacturing same of the present invention, it is possible to improve the load rate of a fragrant material, selectively load a fragrance which can be acquired during the aging process of a mixed fragrant material, maintain the fragrance from the beginning of the loading, and improve the longevity of the fragrance at a uniform strength. In addition, the issue of being harmful to the human body can be resolved by reducing powder flying around, and stability at a high temperature can be improved so as to be applied in various environments.

DETAILED DESCRIPTION OF THE INVENTION

Figure 1:
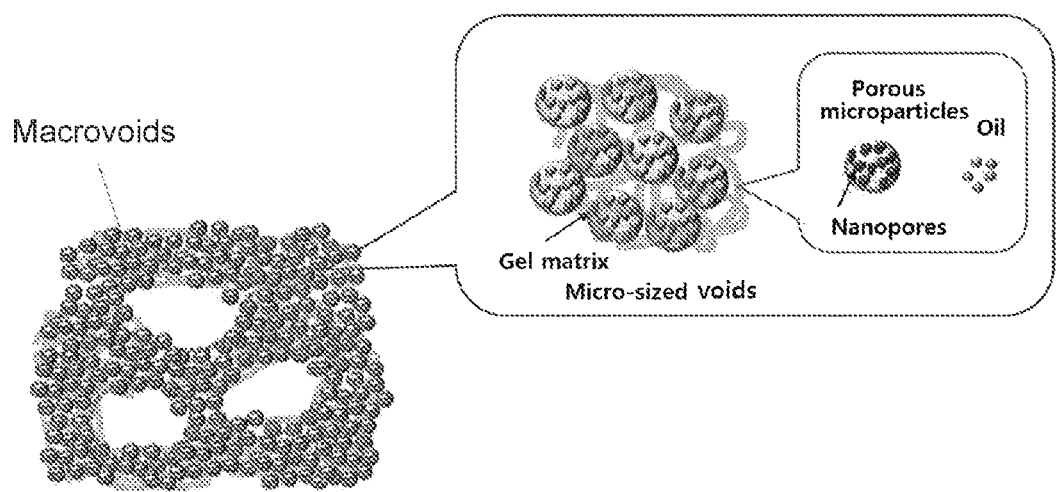
FIG. 1 schematically shows a structure of the composition.

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

Since scent can affect moods and emotions of animals, it is applied in a variety of fields from daily life products to medical treatments. The type of fragrance can be classified according to volatile components and composition ratio of the fragrant material. In addition, since the composition ratio of the volatile component is variable when released for a long period, it tends to give off a different scent from the beginning. In particular, in the case of a natural fragrant material, various kinds of fragrances are mixed for use, but there is a phenomenon (aging) in which the fragrance is denatured due to the change in the composition ratio of the fragrant material over time after combining fragrant materials. In order to load the natural scent during the aging process without change in scent, to maintain the fragrance from the beginning of the loading and to improve the longevity of the fragrance at a uniform strength, there is a need for a composition capable of increasing the load rate of fragrant material and emitting fragrance with a uniform strength.

The present invention is to provide a composition for solving such a problem. In addition, it is intended to provide a solid fragrance composition for improving stability and allowing for free forming of a shape during product processing by supplementing disadvantage such as powder flying.

Hereinafter, the solid fragrance composition and the method of manufacturing the same according to embodiments of the present invention will be described in more detail.

As used herein, the term "matrix" may be described interchangeably with "anchor" or "binder", and refers to a material having a fibrous structure, which exists in an inter-particle space and by which voids can be formed.

As used herein, the term "fragrant material" may be used interchangeably with "fragrance substance" and may include, for example, oil, hydrophilic solution, or a combination thereof.

The term "super absorbent polymer (SAP)" used herein may be used in the same meaning as "super absorbent resin", "Super Absorbency Material (SAM)" and "Absorbent Gel Material (AGM)".

Unless otherwise specified in the disclosure, the expression "to" as used with numerical values means an expression including the corresponding numerical value. Specifically, for example, the expression "1 to 2" means not only including 1 and 2, but also including all numerical values between 1 and 2.

The present invention provides a solid fragrance composition, comprising porous particles having a plurality of pores, a gel matrix, a super absorbent polymer and a fragrant material contained in the pores of the porous particles, wherein the composition has micro-sized voids formed by the gel matrix, and macrovoids formed by the super absorbent polymer which are larger than the micro-sized voids.

When using only porous particles or microparticles to load the fragrant material, disadvantages such as harm to the human body may occur due to powder flying after complete emitting of fragrance. Accordingly, the gel matrix is used to improve high temperature stability and to allow for free forming of a shape and the super absorbent polymer is used to further improve the load rate.

The weight ratio of the porous particle and the gel matrix may affect the load rate and the molding stability. Specifically, when the weight ratio of the gel matrix is excessively increased, the content ratio of the porous particles, which is the main material on which the fragrant material is loaded, decreases, so that the load rate may decrease. On the other hand, when the weight ratio of the gel matrix is excessively decreased, it is difficult to stably bind the porous microparticles to each other, and thus a powder flying phenomenon may occur. Therefore, according to one embodiment, the weight ratio of the gel matrix and the porous particles may be 1:0.1 to 1:30, for example 1:0.4 to 1:30, for example 1:0.4 to 1:3, for example 1:3 to 1:30, for example 1:4 to 1:20, for example 1:3 to 1:19, for example 1:9.

When the content of the super absorbent polymer is excessively small, it may be difficult to sufficiently form macrovoids, and when the content is excessively increased, it may be difficult to maintain a shape of the molded product. Therefore, the composition may contain 0.001 to 20 parts by weight, for example 0.1 to 20 parts by weight, for example 0.5 to 10 parts by weight of the super absorbent polymer based on 100 parts by weight of the total of the gel matrix and the porous particles.

According to one embodiment, the porous particles may include at least one selected from the group consisting of silica, zeolite, activated carbon, and acrylic resin particles. For example, the acrylic resin particles may include poly(methylmethacrylate)(PMMA).

The porous particles are preferably materials harmless to the human body and environments and may further comprise an additional support. The porous particles have a very large surface area due to the formation of nano-pores and form a three-dimensional skeletal structure, so that the fragrant material can be stably loaded without deterioration of fragrance. In addition, the porous particles, which are main components for loading the fragrant material, may serve to prevent deterioration of fragrance by gradually releasing the loaded fragrant material. As such, an average diameter of nanopores of the particles for effective loading, emission, and prevention of deterioration of fragrance may be, for example, 1 to 100 nm, for example, 10 to 100 nm, for example, 20 to 50 nm, and the average particle size (diameter) is 1 to 100 μm, for example, it may be 10 to 100 μm.

In addition, in order to improve the load rate, the porosity of the porous particles may be, for example, 70% or more, for example, 80% or more, for example, 90% or more. The load rate on the porous particles may be calculated according to Equation 1, and may have, for example, 100 to 500%, for example, 200 to 500%.

$$\text{Load rate (\%)} = (\text{maximum weight of loaded fragrant material (g)}/\text{weight of support (g)}) \times 100 \qquad \text{[Equation 1]}$$

In Equation 1, the weight of the support refers to the sum of the weights of the porous particles, the gel matrix, and the super absorbent polymer.

According to one embodiment, the gel matrix may comprise at least one selected from the group consisting of agar, gypsum, silicone rubber, carrageenan, gellan gum and gelatin. The gel matrix is a material that forms voids of a certain size as water evaporates and forms a network structure, and can be replaced or added if it is harmless to the human body.

Specifically, for example, when the gel matrix is gypsum, silicone rubber, or a combination thereof, a weight ratio of the gel matrix and the porous particles may be 1:0.1 to 1:3, for example, 1:0.1 to 1:2.

The gel matrix may have, for example, a fibrous structure and it serves to stably bind porous particles to each other and has a lot of micro-sized voids formed between structures entangled with particles. The average diameter of the micro-sized void in the gel matrix may be, for example, 0.1 to 100 μm, for example, 0.5 to 50 μm, for example, 1 to 20 μm. With such a void size, the micro-sized voids can fix porous particles and serve as a channel for loading and releasing the fragrant material. Moreover, the incorporation of the gel matrix causes no powder flying phenomenon after complete emitting of the fragrant material, so that products can be safely used and the composition can be formed in various shape. The voids having a size of several microns formed by the gel matrix refer to micro-sized pores formed in the process of binding the porous particles by the gel matrix.

Super absorbent polymers can be classified into starch-based super absorbent polymers, cellulose-based super absorbent polymers, and synthetic resin-based super absorbent polymers depending on the raw material. Specifically, the synthetic resin-based super absorbent polymers may be classified into polyacrylic acid salts, polyvinyl alcohol, polyacrylamide and polyoxyethylene. Specifically, for example, it includes a polymer in which acrylonitrile is graft-copolymerized onto starch or cellulose, a block copolymer of acrylic acid and vinyl alcohol, a polymer in which polyvinyl alcohol and polyoxyethylene are crosslinked, a polyacrylic acid-starch graft copolymer, and a polyacrylic acid-polyvinyl alcohol graft copolymer. In addition, the cellulose-based polymer may include, for example, a carboxymethyl cellulose (CMC)-based polymer.

Figure 2:
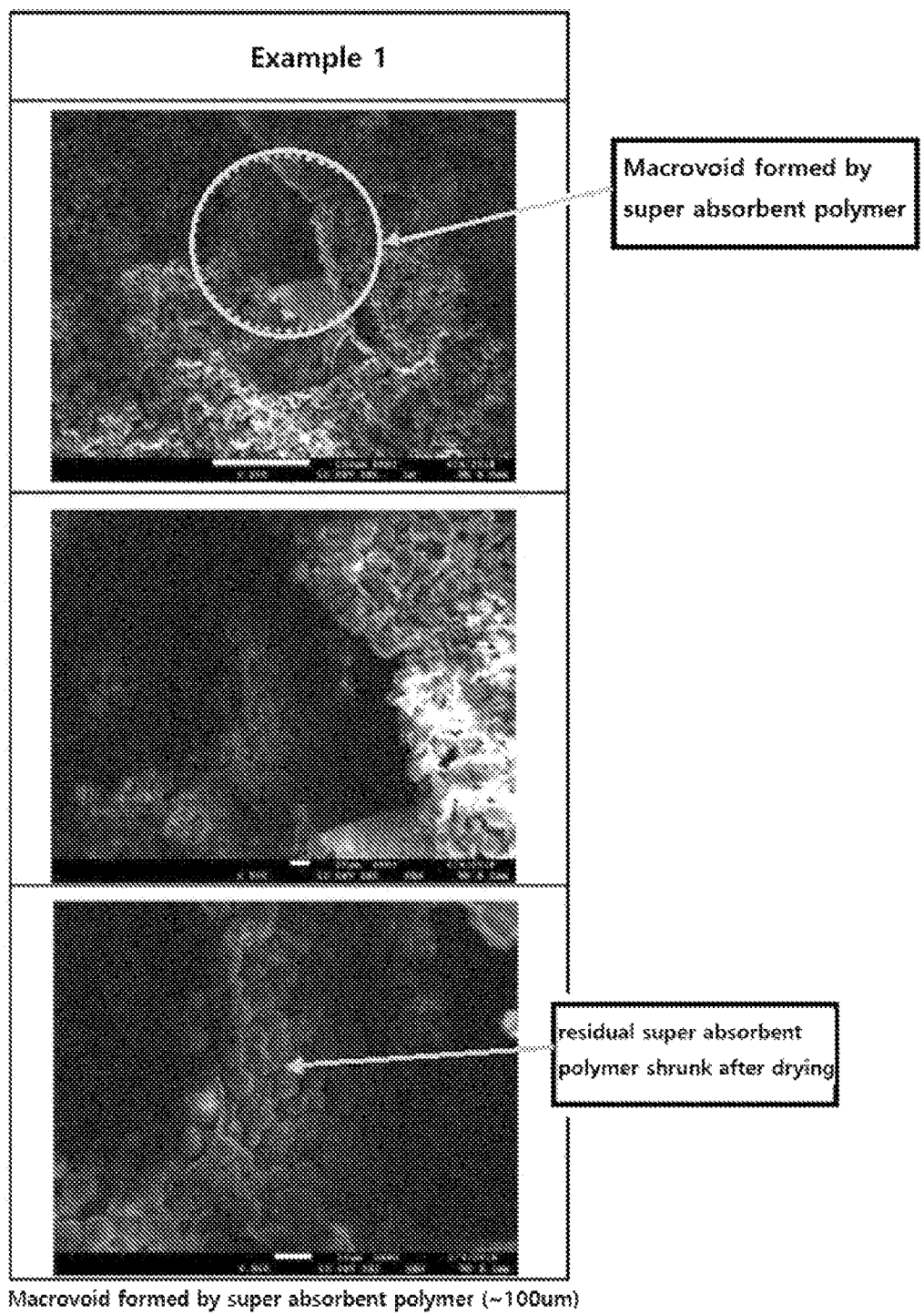
FIG. 2 is a scanning electron microscope (SEM) photograph of the composition according to Example 1.

According to an embodiment, the super absorbent polymer may comprise at least one selected from the group consisting of polyacrylic acid-starch graft copolymer, polyacrylic acid-polyvinyl alcohol graft copolymer, CMC (carboxymethyl cellulose) polymer, and PVA (polyvinyl alcohol) polymer, for example a polyacrylic acid-starch graft copolymer or a polyacrylic acid-polyvinyl alcohol graft copolymer. Super absorbent resin is a material capable of absorbing as much water as hundreds to thousands of times of its own weight, for example, and forming macrovoids in the gel matrix due to volume contraction in the process of drying after absorbing moisture. The voids are formed between the gel matrix structures and, as shown in FIG. 2, super absorbent polymer particles are distributed on the surface of the macrovoids. These voids have, for example, an average diameter of 50 to 500 μm, and serve as a space for storing fragrant materials, so that the load rate can be greatly improved and can serve as a channel for releasing fragrant materials. In particular, in the case of using a gel matrix such as gypsum or silicon rubber, the composition ratio of the gel matrix to the porous microparticles is high, so the macrovoids formed by the super absorbent polymer contribute to a high load rate and serve as a release channel of the fragrant material.

According to one embodiment, the fragrant material may include, for example, aroma essential oil or essential oil, and may include, for example, an extract extracted with a water-soluble solvent. Specific examples of essential oils include lavender, grapefruit, geranium, cinnamon leaves, tea tree, cedarwood, orange, eucalyptus, bergamot, lemon, lime, mandarin, myrrh, neroli, niaouli, peppermint, pine, rosemary, chamomile, ylang-ylang, neem, frankincence, benzoin, helichrysum, phytoncide, rosewood, sandalwood, and the like. In addition, the fragrant material may be diluted with a carrier oil or a solvent. The carrier oil is, for example, one or more selected from the group consisting of grapeseed, evening primrose, rosehip, macadamia nuts, borage, safflower, sesame, St. John's wort oil, sweet almond, avocado, apricot kernel, olive, wheatgerm, calendula, carrot, coconut, hazelnut, jojoba, basil and almond. In addition, the fragrant material may further comprise a solvent and an additive, the solvent may include ethanol, water, glycerin, silicone oil and the like, and the additive may include pigments. In the present invention, the fragrant material is not limited to the main fragrance substances as described above and any conventional vegetable oil may be used without limitation. Other solvents and additives generally used for combining fragrant materials are included without particular limitation.

According to one embodiment, a method for manufacturing a solid fragrance composition may comprise:

1) mixing porous particles and a gel matrix to prepare a mixture;

2) mixing a super absorbent polymer and water to prepare a water-absorbed super absorbent polymer;

3) mixing the water-absorbed super absorbent polymer of 2) with the mixture of 1);

4) injecting the mixture of 3) into a mold and curing it to prepare a molded product;

5) drying the molded product of 4) to form a support having voids formed by removing moisture from the super absorbent polymer; and 6) injecting a fragrant material into the support of 5).

According to one embodiment, the composition contains 0.001 to 20 parts by weight of the super absorbent polymer based on 100 parts by weight of the total of the gel matrix and the porous particles. In addition, a weight ratio of the gel matrix and the porous particles may be 1:0.1 to 1:30, for example 1:0.1 to 1:20, for example 1:3 to 1:30.

The solid fragrance composition of the present invention according to the above method may have a structure in which porous particles are distributed in a gel matrix structure, as shown in FIG. 1. In addition, by loading the fragrant material in the pores of the porous particles and the micro-sized voids of the gel matrix structure and the macrovoids by the super absorbent polymer, it is possible to highly improve the load rate of fragrant materials, provide a sustained-release fragrance, improve persistence of fragrance, and prevent deterioration of the initial scent.

Hereinafter, embodiments of the present invention will be described in detail so that those skilled in the art can easily carry out the present invention. The present invention may, however, be embodied in many different forms and should not be construed as limited to the embodiments set forth herein.

Examples 1 to 5

A solid fragrance composition was prepared according to the composition shown in Table 1.

Porous silica having an average particle diameter of 5 to 15 μm was used as porous particles, and sodium polyacrylate (crosslinking compound, powder form, Sigma Aldrich) was used as a super absorbent polymer.

TABLE 1

| Ex. | Fragrant material | Porous particle | Gel matrix | Super absorbent polymer |
|---|---|---|---|---|
| Example 1 | Lavender essential oil | Silica 9 g (Average pore diameter: <30 nm) | Agar 1 g | 0.1 g |
| Example 2 | Lavender essential oil | Silica 9 g (Average pore diameter: <30 nm) | Agar 1 g | 0.2 g |
| Example 3 | Lavender essential oil | Silica 8 g (Average pore diameter: <30 nm) | Agar 1 g | 0.5 g |
| Example 4 | Lavender essential oil | Silica 5 g (Average pore diameter: <30 nm) | Gypsum 5 g | 0.1 g |
| Example 5 | Lavender essential oil | Silica 3 g (Average pore diameter: <30 nm) | Silicone rubber 7 g | 0.1 g |

Examples 1 to 3

Porous particles were placed in a 70 ml vial, and agar, a super absorbent polymer and 50 g of purified water were added, followed by stirring. After raising the temperature of the vial to 100° C. and stirring for 30 minutes, it was poured into a mold of a certain shape and left at room temperature for at least 1 hour. When the molded product solidified, it was removed from the mold and dried in an oven at 70° C. for 5 hours or more, in this example for 10 hours, to remove moisture to prepare a molded support.

The support was put into a container containing lavender essential oil and left for 10 hours or more, in this example for 24 hours, to sufficiently load the fragrant material.

Example 4

Porous particles were placed in a 70 ml vial, and gypsum (calcium sulfate dihydrate, powder form, Sigma Aldrich), a super absorbent polymer, and 10 g purified water were added and stirred. Then, it was poured into a mold of a certain shape and left at room temperature for at least 1 hour. When the molded product solidified, it was removed from the mold and dried in an oven at 70° C. for 5 hours or more, in this example for 10 hours, to remove moisture to prepare a molded support. In addition, the fragrant material was loaded in the same manner as in Example 1.

Example 5

Porous particles were placed in a 70 ml vial, and 5 g of room-temperature curing silicone rubber (KE-3420, Shin-Etsu Silicone Korea) were added and uniformly mixed. After 10 g of purified water is absorbed in 0.1 g of the super absorbent polymer, the super absorbent polymer in which the purified water is absorbed is added to the vial in which the porous particles and the silicone rubber solution are mixed. The mixed solution is well stirred and poured into a mold of a certain shape and left at room temperature. When the molded product solidified, it was removed from the mold and dried in an oven at 70° C. for 5 hours or more, in this example for 10 hours, to remove moisture to prepare a molded support. In addition, the fragrant material was loaded in the same manner as in Example 1.

FIG. 2 is a scanning electron microscope (SEM) photograph of the composition according to Example 1. As shown in FIG. 2, it is found that macrovoids having a diameter of about 100 μm are formed between the gel matrix structures by the super absorbent polymer (SAP).

In addition, it can be seen that the super absorbent polymer particles are present in the surface portion of the void formed by the super absorbent polymer.

Figure 3:
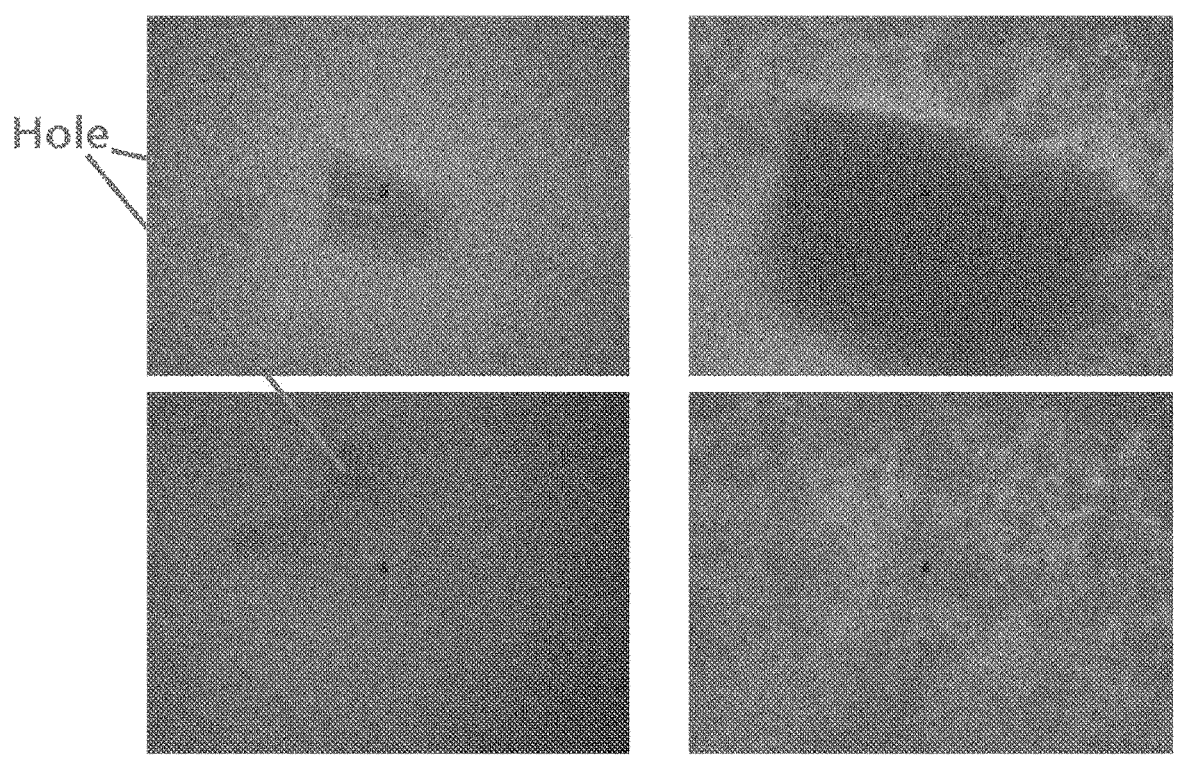
FIG. 3 is a microscope photograph under reflection mode of the composition according to Example 1.

In addition, reflection mode observation photos with a microscope (BX53M/Olympus) for Example 1 are shown in FIG. 3. As shown in FIG. 3, it can be seen that there exist relatively large macrovoids formed by SAP and relatively small micro-sized voids between the silica particles.

Comparative Examples 1 to 3

A solid fragrance composition was prepared according to the composition shown in Table 2.

TABLE 2

| Ex. | Fragrant material | Porous particle | Gel matrix |
|---|---|---|---|
| Comparative Example 1 | Lavender essential oil | — | Ethylene vinyl acetate 8 g |
| Comparative Example 2 | Lavender essential oil | Silica 5 g (Average pore diameter: <30 nm) | Gypsum 5 g |
| Comparative Example 3 | Lavender essential oil | Silica 3 g (Average pore diameter: <30 nm) | Silicone rubber 7 g |

Comparative Example 1

2 g of lavender essential oil was added to a sealed high-pressure vial. 8 g of ethylene vinyl acetate (EVA) (Dupont, Elvax) pellets were added to the vial, and stirred at a speed of 150 rpm for 2 hours while maintaining a temperature of 40° C. and a pressure of 40 cmHg. The above process was repeated by changing the amount of lavender essential oil. The maximum amount when lavender essential oil was completely loaded into the EVA pellets was defined as a load rate.

Comparative Example 2

A composition was prepared in the same manner as in Example 4, except that a super absorbent polymer was included.

Comparative Example 3

A composition was prepared in the same manner as in Example 5, except that a super absorbent polymer was included.

Experimental Example 1: Measurement of Load Rate of Fragrant Material

In order to measure the load rate of the fragrant material, for each composition of Examples and Comparative Examples, the amount of the loaded fragrant material was measured relative to the weight of the support (porous particles, gel matrix, and super absorbent polymer).

The load rate was calculated according to Equation 1, and the results are shown in Table 3.

Load rate (%)=(maximum weight of loaded fragrant material (g)/weight of support (g))×100    [Equation 1]

TABLE 3

| Ex. | Load rate of fragrant material (%) |
|---|---|
| Comparative Example 1 | 20 |
| Comparative Example 2 | 50 |
| Comparative Example 3 | 40 |
| Example 1 | 270 |
| Example 2 | 290 |
| Example 3 | 320 |
| Example 4 | 120 |
| Example 5 | 100 |

As shown in Table 3, it can be seen that all the compositions according to Examples have a load rate of 100% or more. In particular, it is found that the load rate in all Examples increases by at least 16 times compared to Comparative Example 1, which is a conventional solid fragrance composition.

In addition, the load rate of Example 4 was increased by 2.4 times compared to Comparative Example 2, and the load rate of Example 5 was increased by 2.5 times compared to Comparative Example 3, confirming the effect of increasing the load rate according to the inclusion of a super absorbent polymer.

Experimental Example 2: Evaluation of Retention of Initial Scent and Persistence of Fragrance Sensory evaluation was performed according to the criteria shown in Table 4 to confirm the degree of deterioration of the initial scent according to each composition. A sample amount of each composition was taken based on 0.5 g of a fragrant material to have same amount of the fragrant material, and then it was placed in a glass petri dish. After the sample was stored for 15 days at room temperature, an evaluation test for retention of the initial scent was carried out by a panel trained in scent.

TABLE 4

| Retention of initial scent | |
|---|---|
| Grade | |
| 0 | Completely different kind of smell from the initial |
| 1 | Grading the degree of smell difference from to the initial |
| 2 | (The higher the number, the same smell as the initial) |
| 3 | |
| 4 | |
| 5 | Same smell as the initial |

In addition, sensory evaluation was performed according to the criteria shown in Table 5 to evaluate persistence of fragrance. A sample amount of each composition was taken based on 0.5 g of a fragrant material to have same amount of the fragrant material, and then it was placed in a 70 ml vial. The sample was put in a 1 L beaker while it was contained in a vial, and appropriate amount of purified water was filled therein. Then, the temperature was raised on a hot plate by setting at 50° C. When the temperature reached the set temperature, the sample was collected in a 1 L Tedlar bag at a predetermined time while leaving the lid of the sample open. The collected samples were evaluated for persistence of fragrance by a panel trained in scent.

TABLE 5

| | Persistence of fragrance |
|---|---|
| Grade | |
| 0 | Odorless |
| 1 | Smell that can be felt slightly (minimum cognitive concentration) |
| 2 | Weak smell to know what it is |
| 3 | Easily recognizable smell |
| 4 | Irritating smell |
| 5 | Strong smell |

Evaluation results of the retention of initial scent and persistence of fragrance are shown in Table 6.

TABLE 6

| | Retention of initial scent | | Persistence of fragrance | |
|---|---|---|---|---|
| Ex. | Initial | After 15 days | Initial | After 15 days |
| Comparative Example 1 | 5 | 4 | 3 | 2 |
| Comparative Example 2 | 5 | 4 | 5 | 3 |
| Comparative Example 3 | 5 | 4 | 3 | 3 |
| Example 1 | 5 | 4 | 5 | 4 |
| Example 2 | 5 | 4 | 5 | 4 |
| Example 3 | 5 | 4 | 5 | 3 |
| Example 4 | 5 | 4 | 5 | 4 |
| Example 5 | 5 | 4 | 5 | 4 |

As shown in Table 6, it is found that the compositions according to Examples are superior in the persistence of fragrance compared to the compositions of Comparative Examples. In particular, the composition of Example 5 has excellent initial strength of fragrance and the persistence of fragrance, compared to Comparative Example 3. From this, it is found that in the case of a high-density gel matrix such as silicone rubber, macrovoids created by the super absorbent polymer have a great influence on improving the initial strength of fragrance and persistence of fragrance.

Experimental Example 3: Evaluation of High Temperature Stability

A sample amount of each composition was taken based on 0.5 g of a fragrant material to have same amount of the fragrant material, and then it was placed in a 70 ml vial. Each of the samples was evaluated in a convection oven at temperature of 50, 70 and 90° C. according to the criteria shown in Table 7, and the results are shown in Table 8.

TABLE 7

| | Criteria of high temperature stability |
|---|---|
| ◎ | Not melt and flow when stored at 90° C. |
| ○ | Not melt and flow when stored at 70° C. |
| Δ | Not melt and flow when stored at 50° C. |
| NG | Melt and flow to be deformed when stored at 50° C. |

TABLE 8

| Ex. | High temperature stability |
|---|---|
| Comparative Example 1 | ◎ |
| Comparative Example 2 | ◎ |
| Comparative Example 3 | ◎ |
| Example 1 | ◎ |
| Example 2 | ◎ |
| Example 3 | ◎ |
| Example 4 | ◎ |
| Example 5 | ◎ |

Experimental Example 4: Evaluation of Shape Control and Retention

In order to evaluate shape stability of each composition, it was evaluated for powder flying and moldability. A sample amount of each composition was taken based on 0.5 g of a fragrant material to have same amount of the fragrant material, and then it was placed in a 70 ml vial. The sample was placed in a convection oven at 90° C. for 1 day until the fragrant material was sufficiently removed. For each sample from which the fragrant material was removed, powder flying was evaluated according to criteria shown in Table 9, and the results are shown in Table 10.

TABLE 9

| | Criteria of powder flying |
|---|---|
| ◎ | Neither sticking on the surface nor powder flying after removal of fragrant material |
| ○ | Slightly sticking on the surface but no powder flying after removal of fragrant material |
| Δ | Sticking on the surface but no powder flying after removal of fragrant material |
| NG | Powder flying after removal of fragrant material |

TABLE 10

| Ex. | Powder flying | Shape control and retention |
|---|---|---|
| Comparative Example 1 | ◎ | Moldable |
| Comparative Example 2 | ◎ | Moldable |
| Comparative Example 3 | ◎ | Moldable |
| Example 1 | ◎ | Moldable |
| Example 2 | ◎ | Moldable |
| Example 3 | ◎ | Moldable |
| Example 4 | ◎ | Moldable |
| Example 5 | ◎ | Moldable |

Summarizing the above results, for the compositions according to Comparative Examples 1 to 3, the load rate of fragrance was low and the initial strength of fragrance and persistence of fragrance rapidly decreased. On the other hand, according to an embodiment of the present invention, it is possible to provide a composition that remarkably improves the load rate, retention of initial scent and persistence of fragrance while satisfying both high-temperature stability and shape retention characteristics.

Therefore, a solid fragrance with improved utility and stability can be freely processed into a required shape and easily applied to various fields.

The above description is merely illustrative of the technical idea of the present invention, and those of ordinary skill in the art to which the present invention pertains can make various modifications and variations without departing from the essential characteristics of the present invention. In addition, the embodiments disclosed in the present invention are not intended to limit the technical idea of the present invention, but to explain the technical idea, and the scope of the technical idea of the present invention is not limited by these embodiments. The scope of protection of the present invention should be interpreted by the following claims, and all technical ideas within the scope equivalent thereto should be construed as being included in the scope of the present invention.

What is claimed is:

1. A solid fragrance composition, comprising porous particles having a plurality of nanopores, a gel matrix, a super absorbent polymer, and a fragrant material contained in the nanopores of the porous particles,
wherein the composition contains 0.001 to 20 parts by weight of the super absorbent polymer based on 100 parts by weight of the total of the gel matrix and the porous particles, and
wherein the composition has micro-sized voids formed by the gel matrix, and macrovoids formed by the super absorbent polymer which are larger than the micro-sized voids.

2. The solid fragrance composition according to claim 1, wherein a weight ratio of the gel matrix and the porous particles is 1:0.1 to 1:30.

3. The solid fragrance composition according to claim 1, wherein the porous particles are at least one selected from the group consisting of silica, zeolite, activated carbon and acrylic resin particles.

4. The solid fragrance composition according to claim 1, wherein the gel matrix comprises at least one selected from the group consisting of agar, gypsum, silicone rubber, carrageenan, gellan gum and gelatin.

5. The solid fragrance composition according to claim 1, wherein the super absorbent polymer comprises at least one selected from the group consisting of polyacrylic acid-starch graft copolymer, polyacrylic acid-polyvinyl alcohol graft copolymer, CMC (carboxymethyl cellulose) polymer, and PVA (polyvinyl alcohol) polymer.

6. The solid fragrance composition according to claim 2, wherein a weight ratio of the gel matrix and the porous particles is 1:0.1 to 1:3 and the gel matrix is gypsum, silicone rubber, or a mixture thereof.

7. The solid fragrance composition according to claim 1, wherein an average particle size of the porous particle is 1 to 100 μm.

8. The solid fragrance composition according to claim 1, wherein the nanopores of the porous particles has an average diameter of 1 to 100 nm.

9. The solid fragrance composition according to claim 1, wherein the micro-sized voids formed by the gel matrix has an average diameter of 0.1 to 100 μm.

10. The solid fragrance composition according to claim 1, wherein the macrovoids formed by the super absorbent polymer has an average diameter of 50 to 500 μm.

11. The solid fragrance composition according to claim 1, wherein the micro-sized voids and the macrovoids have the fragrant material contained therein.

12. A method for manufacturing a solid fragrance composition, comprising:
1) mixing porous particles and a gel matrix to prepare a mixture;
2) mixing a super absorbent polymer and water to prepare a water-absorbed super absorbent polymer;
3) mixing the water-absorbed super absorbent polymer of 2) with the mixture of 1);
4) injecting the mixture of 3) into a mold and curing it to prepare a molded product;
5) drying the molded product of 4) to form a support having voids formed by removing moisture from the super absorbent polymer; and
6) injecting a fragrant material into the support of 5),
wherein the composition contains 0.001 to 20 parts by weight of the super absorbent polymer based on 100 parts by weight of the total of the gel matrix and the porous particles, and wherein the support comprises micro-sized voids formed by the gel matrix and macrovoids formed by the super absorbent polymer which are larger than the micro-sized voids.

13. The method for manufacturing a solid fragrance composition according to claim 12, wherein the load rate of the fragrant material according to Equation 1 is 100 to 500%.

$$\text{Load rate (\%)} = (\text{maximum weight of loaded fragrant material (g)}/\text{weight of support (g)}) \times 100. \quad [\text{Equation 1}]$$

* * * * *